United States Patent [19]
Bosslet et al.

[11] Patent Number: 5,908,790
[45] Date of Patent: Jun. 1, 1999

[54] METHODS FOR REMOVING HEAVY METALS FROM AQUEOUS SOLUTIONS AND FOR ANALYSIS

[75] Inventors: Klaus Bosslet; Peter Hermentin; Gerhard Seemann, all of Marburg, Germany

[73] Assignee: Behring Diagnostics GmbH, Marburg, Germany

[21] Appl. No.: 08/463,087

[22] Filed: Jun. 5, 1995

Related U.S. Application Data

[62] Division of application No. 08/440,354, May 12, 1995, which is a continuation of application No. 08/327,846, Oct. 24, 1994, abandoned, which is a continuation of application No. 08/132,231, Oct. 6, 1993, abandoned, which is a continuation of application No. 08/013,166, Feb. 2, 1993, abandoned, which is a continuation of application No. 07/664,789, Mar. 5, 1991, abandoned.

[30] Foreign Application Priority Data

Mar. 7, 1990 [DE] Germany .............................. 40 07 079

[51] Int. Cl.⁶ .................................................. G01N 33/53
[52] U.S. Cl. ........................... 436/512; 436/538; 435/7.1; 435/345; 530/388.1; 530/388.9; 530/413; 424/78.34; 424/609
[58] Field of Search ..................................... 436/512, 538; 424/130.1; 530/387.1, 388.1, 388.9, 413; 435/7.1, 345

[56] References Cited

U.S. PATENT DOCUMENTS 4,722,892  2/1988  Meares et al. .............................. 435/7

OTHER PUBLICATIONS

J.L. Cordell et al., "Immunoenzymatic Labeling of Monoclonal Antibodies Using Immune Complexes of Alkaline Phosphatase and Monoclonal Anti–alkaline Phosphatase (APAAP Complexes)," *The Journal of Histochemistry and Cytochemistry*, 32:219–229 (1984).

M.W. Brechbiel, "Synthesis of 1–(p–Isothiocyanatobenzyl) Derivatives of DTPA and EDA. Antibody Labeling and Tumor–Imaging Studies," *Inorganic Chemistry*, 25(16):2272–2781 (1986).

M. Shulman et al., "A Better Cell Line for Making Hybridomas Secreting Specific Antibodies," *Nature*, 276:269–270 (1978).

R. Orlandi et al., "Cloning Immunoglobulin Variable Domains for Expression by the Polymerase Chain Reaction," *Proc. Nat'l. Acad. Sci.*, USA, 86:3833–3837 (May 1989).

D.T. Reardan et al., "Antibodies against metal chelates," *Nature*, 316:265–267 (1985).

Goding, *Monoclonal Antibodies*, pp. 76–88 (1986).

R.J. Robins, "The Measurement of Low Molecular–Weight, Non–Immunogenic Compounds by Immunoassay," *Immunology in Plant Science*, pp. 86–141 (1986).

Yamauchi et al., J. Clin. Invest. 56:958–969 (1975).

*Primary Examiner*—Paula K. Hutzell
*Assistant Examiner*—Julie E. Reeves
*Attorney, Agent, or Firm*—Finnegan, Henderson, Farabow, Garrett & Dunner, L.L.P.

[57] ABSTRACT

The invention relates to monoclonal antibodies (mAB) which bind to water-soluble complexones such as ethylenediamine tetraacetate (EDTA) or diethylenetriamine pentaacetate (DTPA) with high specificity and avidity and retain their high avidity and specificity for these complexones after complexing of EDTA or DTPA with metal ions. These mAB can therefore be used, e.g. coupled on filters or other supports, for removing toxic heavy metals which are complexed with EDTA or DTPA. Furthermore, these mAB are suitable as components of immunoassays (RIA, ELISA etc.) for the quantitative determination of EDTA or DTPA in aqueous solutions.

12 Claims, No Drawings

METHODS FOR REMOVING HEAVY METALS FROM AQUEOUS SOLUTIONS AND FOR ANALYSIS

This is a division of application Ser. No. 08/440,354, filed May 12, 1995, which is a continuation application of application Ser. No. 08/327,846, filed Oct. 24, 1994, now abandoned, which is a continuation application of application Ser. No. 08/132,231, filed Oct. 6, 1993, now abandoned, which is a continuation application of application Ser. No. 08/013,166, filed Feb. 2, 1993, now abandoned, which is a continuation application of application Ser. No. 07/664,789, filed Mar. 5, 1991, now abandoned.

The invention relates to monoclonal antibodies (mAB) which bind to water-soluble complexones such as ethylenediamine tetraacetate (EDTA) or diethylenetriamine pentaacetate (DTPA) with high specificity and avidity and retain their high avidity and specificity for these complexones after complexing of EDTA or DTPA with metal ions. These mAB can therefore be used, e.g. coupled on filters or other supports, for removing toxic heavy metals which are complexed with EDTA or DTPA. Furthermore, these mAB are suitable as components of immunoassays (RIA, ELISA etc.) for the quantitative determination of EDTA or DTPA in aqueous solutions.

Heavy metals which are linked to complexones such as EDTA are a serious danger in the field of drinking water supply. For this reason, the fast, exact and quantitative determination of the concentration of EDTA is of as great an importance as the removal of EDTA metal complexes from waste waters or drinking water.

In our project for obtaining mAB against hydrophilic complexones for the purpose of tumor therapy, we have surprisingly been successful in generating mAB which have a high avidity against both noncomplexed and metal-complexed EDTA or DTPA.

The mAB were prepared as follows. As is explained individually in the examples, isothiocyanatobenzyl-DTPA was coupled to human serum albumin and complexed with yttrium ions as hapten. This hapten-"carrier"-complex was subsequently used for immunizing suitable mice and the spleens of the mice with the highest anti-DTPA antibody titers were fused with a suitable myeloma cell line. The resulting hybridomas were tested in the specific enzyme-linked immunoassay (ELISA) described below.

The ELISA comprised a solid phase which was loaded with a solution containing human serum albumin (HSA)-benzyl-DTPA. The supernatant which was to be tested and contained the mAB was preincubated with free complexone or the metal ion complex thereof, and its binding to the specific solid phase was measured. For this purpose, an enzyme amplification system which is coupled to an anti-mouse-immunoglobulin antibody was used. The details of this method are described in Examples 2 and 3.

By means of this test system, mAB which have the properties described in Table I were obtained.

These mAB, in contrast to many other anti-DTPA/EDTA mAB, do not bind to normal human tissue as was determined on cryopreserved tissues by means of the APAAP technique (Cordell et al., J. Histochem. Cytochem. 32: 219, 1984). It is thus possible to employ these mAB in vivo in the field of diagnosis and therapy.

The complexones DTPA and EDTA in noncomplexed and in complexed form (Example 4) were used as competitors. Additionally, the structurally related compounds transaconitic acid and 1,2-diaminoethane were used as inhibitors (see Tab. I). The excess amounts of competitor presented in Tab. I, which lead to a 50% inhibition of the mAB antigen binding, show that the mAB listed have a strong binding to both noncomplexed EDTA or DTPA and EDTA or DTPA complexed with metal ions. These characteristics make it possible to use the mAB, e.g. coupled on filters or other solid supports, for removing both noncomplexed EDTA or DTPA and EDTA-metal ion or DTPA-metal ion complexes from liquids. Precipitation reactions of mAB-/EDTA-metal ion complexes are likewise suitable for removing the toxic metal ions.

A particularly suitable mAB for this use is mAB BW 2050/535 whose interaction with EDTA and the complexes thereof is particularly strong.

The invention therefore relates to an mAB with a high affinity against those EDTA or DTPA complexed with metal ions and noncomplexed EDTA or DTPA, to a process for the preparation thereof and to the use thereof as component of a diagnostic or therapeutic, or for the removal of toxic metal ions.

The invention is furthermore described in more detail in the examples and contained in the patent claims.

EXAMPLE 1

Preparation of EDTA- or DTPA-specific mAB

Isothiocyanatobenzyl-DTPA was, as hapten, covalently coupled to human serum albumin (HSA) as carrier according to the method described by N. W. Brechbiel et al., Inorganic Chemistry 25: 2772–2781 (1986) with a degree of derivatization of 19 benzyl-DTPA molecules per HSA molecule. 20 $\mu$g of this hapten-carrier complex, into which unlabeled $YCl_3$ was complexed, were injected s.c. into BALB/c mice on day 0 with Freund's adjuvant, on day 7 and day 14 with incomplete Freund's adjuvant and on day 21 with PBS. On day 24 the spleens of the mice with the highest anti-DTPA antibody titers were fused with the SP2/0-Ag14 myeloma cell line (Shulman et al., Nature 276: 269 (1976)). Resulting hybridomas were tested for the production of mAB with high affinity in a specific ELISA (Example 2).

EXAMPLE 2

Quantitative inhibition ELISA for mAB by DTPA or EDTA complexes

Divisible 96-well polystyrene microtiter plates (U-shape) type B. supplied by Nunc, No. 4-60445 were employed as support material. The assay was carried out according to the following protocol.

(1) 50 $\mu$l of Y benzyl-DTPA-HSA 19-conjugate with a concentration of 1 $\mu$g of conjugate per ml of PBS, pH 7.2, are pipetted per well and incubated overnight at room temperature (RT)

(2) The supernatant is aspirated off and washing is carried out 3× using 0.05 M tris-citrate buffer, pH 7.4 (wash solution 1); (1× washing = introduce 250 $\mu$l of wash solution per well, leave to stand for 2 min, aspirate off).

(3) If the microtiter plate is not required directly, it is left standing (opening down) on cellulose at RT overnight. Then the plate is heat-sealed in films together with balance desiccators (supplied by Gaplast, Postfach 529, 8100 Garmisch-Partenkirchen). Under these conditions, the plates can be kept for at least 8 weeks at +4° C.

(4) 250 $\mu$l of blocking solution per well are applied and incubated at 37° C. for 30 min.

(5) During the blocking, the preincubation of the diluted hybridoma supernatant with the competitor is carried out (see Example 3 or Example 6).

(6) 50 μl of the hybridoma supernatants which are to be tested and have been appropriately prediluted and pre-incubated are applied per well and incubated at room temperature for 30 min.
(7) Washing is subsequently carried out 3× using wash solution 2.
(8) Then 50 μl of goat anti-mouse-IgG$_1$ antibody which has been diluted 1:500 in blocking solution and is labeled with alkaline phosphatase are applied per well and incubated at room temperature for 30 min.
(9) Washing is then carried out 3× using wash solution for Enzygnost$^R$ (Behringwerke AG).
(10) Subsequently, 50 μl of 0.1 mM NADP are added.
(11) Incubation is then carried out at room temperature for 30 min.
(12) During the incubation with NADP, the amplifier system is prepared as follows:
per plate are added 2 parts of p-iodo-nitrotetrazolium violet (INT) and 1 part of PBS, pH 7.2, furthermore 1 part of diaphorase, and 1 part of ADH is furthermore pipetted into the mixture.
(13) 50 μl of amplifier system are added per well.
(14) In the case of a clear change in color from transparent to red, the reaction is stopped by 100 μl of a 0.1 N $H_2SO_4$ solution per well.
(15) The extinctions are measured at 492 nm in the TITERTEK$^R$ MULTISCAN. 50 μl of NADP together with 50 μl of amplifier solution and 100 μl of 0.1 N $H_2SO_4$ are employed as blank value.

The following reagents were used:
NADP—supplied by Sigma, order no. N-0505
INT—supplied by Sigma, order no. I-8377
ADH—supplied by Sigma, order no. A-3263
DIAPHORASE—supplied by Sigma, order no. D-2381
Wash solution 2—supplied by Behring, order no. OSEW96, contains Tween/PBS
Blocking solution: a 3% casein solution is prepared in PBS, pH 7.2, by adding casein and stirring for 30 minutes, and the pH is adjusted to 7.4. Then particles are centrifuged off at 4000 rpm for 10 min.
Goat anti-mouse-IgG$_1$ antibody which has been diluted and is labeled with alkaline phosphatase (supplied by Southern Biotechnology Associates, Cat. No. 1080-04)
Preparation of 0.1 mM NADP:
Dissolve 7.65 mg of NADP in 100 ml of 20 mM Tris, 0.1 mM MgSO$_4$, pH 9.5; the solution can be stored for several months at −20° C.
Preparation of INT (p-iodonitrotetrazolium violet):
Dilute 2.5 mg/ml of 30% ethanol in an ultrasonic bath; always prepare freshly.
Preparation of diaphorase:
1 mg of diaphorase/ml of PBS, pH 7.2, is stored in portions at −20° C.
Preparation of alcohol dehydrogenase:
0.5 mg of ADH/ml of PBS, pH 7.2, is stored in portions at −20° C.

EXAMPLE 3

Preincubation of the hybridoma supernatant with the competitor

The mouse-IgG concentration in the hybridoma supernatants can be determined by means of commercially available quantitative ELISA systems and is state of the art.

With reference to the determination of the concentration in the ELISA, the hybridoma supernatants are diluted to 1.25 μg/ml in PBS without $Ca^{++}$ and $Mg^{++}$.

Conversion of grams into moles: 150,000 g=1 mole of mAB 1.25 μg=8.33×10$^{-12}$ mole In order to have a 1+1 ratio of mAB and inhibitor, 10 μl of inhibitor with a concentration of 8.33×10$^{-12}$ mole/200 μl which had been increased a factor of 5 were added to 50 μl of hybridoma supernatant with a concentration of 8.33×10$^{-12}$ mole/ml.

The hybridoma supernatant is incubated for 30 min with a 100,000 fold, 50,000 fold, 10,000 fold, 5,000 fold, 1,000 fold and 100 fold excess of competitor at room temperature. 50 μl thereof are pipetted into the ELISA (see Example 2, item 6).

EXAMPLE 4

Generation of the DTPA or EDTA complexes

The complex constant of DTPA or EDTA in relation to the metal ions shown in Table I is extremely high so that a complete saturation is to be expected in the case of an equimolar mixture of DTPA or EDTA with these metal ions. The appropriate metal ions were therefore incubated with the DTPA or EDTA in a 3 fold molar excess. As an example, 170 μl of a 10 mM cadmium sulfate solution in double-distilled water (see Example 5) were incubated at room temperature with 30 μl of a 0.028 molar DTPA stock solution in double-distilled water for 5 min. Admixing 10 μl of this competitor solution to the hybridoma supernatant leads to a 100,000 fold excess of competitor over the mAB contained in the hybridoma supernatant. Lower ratios of competitor to mAB were achieved by diluting the competitor solution in the particular salt ion solution according to the desired molar excess (see Example 3).

EXAMPLE 5

Source and relevant physicochemical parameters of the metal ions used 10 mmolar solutions of the following metal ions were prepared in double-distilled water:

| | |
|---|---|
| Manganese chloride MW 161.88 supplied by Merck, No. 5934 | Ionic radius of Mn: 80 pm |
| Cadmium sulfate MW 256.5 supplied by Riedel de Haen No. 31145 | Ionic radius of Cd: 97 pm |
| Zinc chloride MW 136.28 supplied by Merck, No. 8816 | Ionic radius of Zn: 74 pm |
| Copper sulfate MW 159.61 supplied by Riedel de Haen No. 31294 | Ionic radius of Cu: 96 pm |
| Yttrium chloride MW 303.36 supplied by Aldrich No. 20,491–9 | Ionic radius of Y: 92 pm |
| Lead (II) nitrate MW 331.20 supplied by Riedel de Haen No. 31137 | Ionic radius of Pb: 120 pm |

EXAMPLE 6

Competitive enzyme immunoassay for determining the EDTA or DTPA concentration in aqueous solvents In the quantitative inhibition ELISA described in Example 2, an aqueous sample (50 μl) having an unknown EDTA content to be determined is added instead of the defined amounts of competitor (lines 26–28, step 5). The assay is further carried out as described in Example 2, step 6-15. The reduction of the extinction is proportional to the concentration of EDTA or DTPA in the unknown sample. After establishing a calibration plot by adding defined EDTA or DTPA concentrations and appropriate predilution of the unknown sample to be tested, the EDTA or DTPA concentration in the unknown sample can be determined quantitatively.

EXAMPLE 7

Description of the particularly suitable mAB BW 2050/535

The $V_H$ and $V_L$ genes of mAB BW 2050/535 have been cloned according to the method described by Orlandi et al. (Proc. Natl. Acad. Sci. U.S.A. 86, 3833 (1989)) and were then sequenced. The nucleotide and the amino acid sequences of the $V_L$ gene of mAB BW 2050/535 are dipicted in SEQ ID NO:1 and SEQ ID NO:2, and of the $V_H$ gene in SEQ ID NO:3 and SEQ ID NO:4. The sequence of the $V_H$ gene comprises the coding sequence for amino acids 4 through 110 of the mature protein. The sequence of the $V_L$ gene comprises the coding sequence for amino acids 3 through 106 of the mature protein.

The amino acids are designated in three letter code.

TABLE 1

Quantitative inhibition assay of mAB by DTPA or EDTA complexes
Molar excess of <u>competitor</u>, which leads to 50% inhibition of binding to the solid phase antigen

| MAk-Nr. | DTPA-Y | DTPA | DTPA-Mn | DTPA-Cd | DTPA-Zn | DTPA-Cu | DTPA-Pb | 1,2-diamino-ethane |
|---|---|---|---|---|---|---|---|---|
| 2050/174 | $10^4$ | $10^3$ | $10^2$ | $10^2$ | $5 \times 10^3$ | $5 \times 10^3$ | $10^3$ | no inhibition up to $10^5$ |
| 2050/531 | $5 \times 10^4$ | $10^3$ | $10^2$ | $10^2$ | $5 \times 10^3$ | $5 \times 10^3$ | $5 \times 10^3$ | no inhibition up to $10^5$ |
| 2050/532 | $5 \times 10^4$ | $10^3$ | $10^2$ | $10^2$ | $5 \times 10^3$ | $5 \times 10^3$ | $5 \times 10^3$ | no inhibition up to $10^5$ |
| 2050/534 | $5 \times 10^4$ | $10^3$ | $10^2$ | $10^2$ | $5 \times 10^3$ | $5 \times 10^3$ | $5 \times 10^3$ | no inhibition up to $10^5$ |
| 2050/535 | $10^4$ | $10^2$ | $10^2$ | $10^2$ | $10^3$ | $10^3$ | $10^3$ | no inhibition up to $10^5$ |

| mAb no. | trans-aconitic acid | EDTA-Y | EDTA | EDTA-Mn | EDTA-Cd | EDTA-Zn | EDTA-Cu | EDTA-Pb |
|---|---|---|---|---|---|---|---|---|
| 2050/174 | no inhibition up to $10^5$ | $10^2$ | $10^3$ | $10^3$ | $10^3$ | $10^3$ | $10^3$ | $5 \times 10^3$ |
| 2050/531 | no inhibition up to $10^5$ | $10^3$ | $10^3$ | $10^3$ | $10^3$ | $10^3$ | $10^2$ | $10^5$ |
| 2050/532 | no inhibition up to $10^5$ | $10^2$ | $10^3$ | $10^3$ | $10^3$ | $10^2$ | $5 \times 10^3$ | $10^5$ |
| 2050/534 | no inhibition up to $10^5$ | $10^2$ | $10^3$ | $10^2$ | $10^2$ | $10^3$ | $10^3$ | $5 \times 10^3$ |
| 2050/535 | no inhibition up to $10^5$ | $10^2$ | $10^2$ | $10^2$ | $10^2$ | $10^2$ | $10^2$ | $10^2$ |

We claim:

1. A method for purifying an aqueous liquid contaminated with metal ions comprising
   (a) coupling a monoclonal antibody (mAb) to a solid support to form a coupled mAb;
   (b) contacting the coupled mAb with said aqueous liquid to form mAb-EDTA-metal ion complexes or mAb-DTPA-metal ion complexes; and
   (c) removing said mAb-EDTA-metal ion complexes or mAb-DTPA-metal ion complexes from said aqueous liquid, wherein the mAb
      (i) binds ethylenediamine tetraacetate (EDTA) with about the same affinity as the mAb binds EDTA complexed to a metal ion, or
      (ii) binds diethylenetriamine pentaacetate (DTPA) with about the same affinity as the mAb binds DTPA complexed to a metal ion,
      wherein the metal ion is manganese, cadmium, zinc, copper, yttrium or lead, and
      wherein the affinity is determined to be about the same when excess amount of competitor which leads to a 50% inhibition of mAb-antigen binding is about the same order of magnitude for both complexed and non-complexed EDTA or DTPA.

2. The method of claim 1 wherein the mAb is produced by a method comprising immunization with either isothiocyanatobenzyl-DTPA coupled to human serum albumin (HSA) or isothiocyanatobenzyl-EDTA coupled to HSA.

3. The method of claim 1 wherein the mAb to is identified by competition ELISA with HSA-benzyl-DTPA or HSA-benzyl-EDTA.

4. The method of claim 1 wherein the mAb has heavy and light variable chain domains encoded by polynucleotides comprising SEQ ID NO: 1 and 3, respectively.

5. The method of claim 1 wherein the mAb has heavy and light variable chain domains comprising SEQ ID NO: 2 and 4, respectively.

6. The method of claim 1 wherein the mAb
   (i) binds ethylenediamine tetraacetate (EDTA) with about the same affinity as the mAb binds EDTA complexed to metal ions, or
   (ii) binds diethylenetriamine pentaacetate (DTPA) with about the same affinity as the mAb binds DTPA complexed to metal ions,
   wherein the metal ions are manganese, cadmium, zinc, copper, yttrium and lead, and
   wherein the affinity is determined to be about the same when excess amount of competitor which leads to a 50% inhibition of mAb-antigen binding is about the same order of magnitude for both complexed and non-complexed EDTA or DTPA.

7. A method for quantitative determination of EDTA-metal ion complex concentration or DTPA-metal ion complex concentration in an aqueous liquid comprising an immunoassay comprising:
   (a) coupling a monoclonal antibody (mAb) with a solid support to form a coupled mAb;
   (b) contacting the coupled mAb with said aqueous liquid to form mAb-EDTA-metal ion complexes or mAb-DTPA-metal ion complexes; and
   (c) determining the concentration by measuring the amount of mAb-EDTA-metal ion complexes or mAb-DTPA-metal ion complexes formed in step (b), wherein the mAb
      (i) binds ethylenediamine tetraacetate (EDTA) with about the same affinity as the mAb binds EDTA complexed to a metal ion, or
      (ii) binds diethylenetriamine pentaacetate (DTPA) with about the same affinity as the mAb binds DTPA complexed to a metal ion,
      wherein the metal ion is manganese, cadmium, zinc, copper, yttrium or lead, and
      wherein the affinity is determined to be about the same when excess amount of competitor which leads to a 50% inhibition of mAb-antigen binding is about the same order of magnitude for both complexed and non-complexed EDTA or DTPA.

8. The method of claim 7 wherein the mAb is produced by a method comprising immunization with either isothiocyanatobenzyl-DTPA coupled to human serum albumin (HSA) or isothiocyanatobenzyl-EDTA coupled to HSA.

9. The method of claim 7 wherein the mAb is identified by competition ELISA with HSA-benzyl-DTPA or HSA-benzyl-EDTA.

10. The method of claim 7 wherein the mAb has heavy and light variable chain domains encoded by polynucleotides comprising SEQ ID NO: 1 and 3, respectively.

11. The method of claim 7 wherein the mAb has heavy and light variable chain domains comprising SEQ ID NO: 2 and 4, respectively.

12. The method of claim 7, wherein the mAb
(i) binds ethylenediamine tetraacetate (EDTA) with about the same affinity as the mAb binds EDTA complexed to metal ions, or
(ii) binds diethylenetriamine pentaacetate (DTPA) with about the same affinity as the mAb binds DTPA complexed to metal ions,
wherein the metal ions are manganese, cadmium, zinc, copper, yttrium and lead, and
wherein the affinity is determined to be about the same when excess amount of competitor which leads to a 50% inhibition of mAb-antigen binding is about the same order of magnitude for both complexed and non-complexed EDTA or DTPA.

* * * * *

UNITED STATES PATENT AND TRADEMARK OFFICE
CERTIFICATE OF CORRECTION

PATENT NO. : 5,908,790
DATED : June 01, 1999
INVENTOR(S) : Klaus Bosslet et al.

It is certified that error appears in the above-identified patent and that said Letters Patent is hereby corrected as shown below:

Claim 3, column 9, line 50, after "mAb", delete "to".

Signed and Sealed this

Thirtieth Day of November, 1999

Attest:

Q. TODD DICKINSON

Attesting Officer

Acting Commissioner of Patents and Trademarks

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 318 base pairs
      (B) TYPE: nucleic acid
      (C) STRANDEDNESS: single
      (D) TOPOLOGY: linear (ii) MOLECULE TYPE: DNA (genomic)

(xi) SEQUENCE DESCRIPTION: SEQ ID NO:1:

```
CAGCTGACTC AGGAATCTGC ACTCACCACA TCACCTGGTG AAACAGTCAC ACTCACTTGT      60

CGCTCAAGTA CTGGGGCTGT TACAACTAGT AACTATGCCA CCTGGGTCCA AGAAAAACCA    120

GATCATTTAT TCACTGGTCT AATAGGTGGT ACCAAGAACC GAGCTCCGGG TGTTCCTGCC    180
```

```
AGATTCTCAG GCTCCCTGAT TGGAGACAAG GCTGCCCTCA CCATCACAGG GGCACAGACT      240

GAGGATGAGG CAATATATTT CTGTGCTCTA TGGTACAGCA ACCACTGGGT GTTCGGTGGA      300

GGGACCAAGC TGAAGATC                                                    318
```

(2) INFORMATION FOR SEQ ID NO:2:

(i) SEQUENCE CHARACTERISTICS:
        (A) LENGTH: 106 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:2:

```
Gln Leu Thr Gln Glu Ser Ala Leu Thr Thr Ser Pro Gly Glu Thr Val
 1               5                  10                  15

Thr Leu Thr Cys Arg Ser Ser Thr Gly Ala Val Thr Thr Ser Asn Tyr
             20                  25                  30

Ala Thr Trp Val Gln Glu Lys Pro Asp His Leu Phe Thr Gly Leu Ile
         35                  40                  45

Gly Gly Thr Lys Asn Arg Ala Pro Gly Val Pro Ala Arg Phe Ser Gly
     50                  55                  60

Ser Leu Ile Gly Asp Lys Ala Ala Leu Thr Ile Thr Gly Ala Gln Thr
65                  70                  75                  80

Glu Asp Glu Ala Ile Tyr Phe Cys Ala Leu Trp Tyr Ser Asn His Trp
                 85                  90                  95

Val Phe Gly Gly Gly Thr Lys Leu Lys Ile
                100                 105
```

(2) INFORMATION FOR SEQ ID NO:3:

(i) SEQUENCE CHARACTERISTICS:
        (A) LENGTH: 329 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:3:

```
CTGCAGCAGT CTGGGGCAGA GCTTGTGAAG CCAGGGGCCT CAGTCAAGTT GTCCTGCACA      60

GCTTCTGGCT TAAACATTAA AGACACCTAT ATAAACTGGG TGAAGCAGAG GCCTGAACAG     120

AAGGCCTGGA GTGGATTGGA AGGATTGGTC CTGCGAATGG TAATACTAAA TATGACCCGA     180

AGTTCCAGGG CAAGGCCACT TTAACAGCAG ACACATCCTC CAACACAGCC TACCTACAAC     240

TCAGCAGCCT GACATCTGAG GACACTGCCG TCTATTACTG TTCTAGAAGA TGGTTCTTTC     300

TTTACTGGGG CCAAGGGACC ACGGTCACC                                        329
```

(2) INFORMATION FOR SEQ ID NO:4:

(i) SEQUENCE CHARACTERISTICS:
        (A) LENGTH: 108 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:4:

```
Leu Gln Gln Ser Gly Ala Glu Leu Val Lys Pro Gly Ala Ser Val Lys
 1               5                  10                  15
```

```
         Leu Ser Cys Thr Ser Gly Leu Asn Ile Lys Asp Thr Tyr Ile Asn Trp
                     20              25                  30

Val Lys Gln Arg Pro Glu Gln Gly Leu Glu Trp Ile Gly Arg Ile Gly
                     35              40                  45

Pro Ala Asn Gly Asn Thr Lys Tyr Asp Pro Lys Phe Gln Gly Lys Ala
                 50              55              60

Thr Leu Thr Ala Asp Thr Ser Ser Asn Thr Ala Tyr Leu Gln Leu Ser
         65              70              75                          80

Ser Leu Thr Ser Glu Asp Thr Ala Val Tyr Tyr Cys Ser Arg Arg Trp
                         85              90                      95

Phe Phe Leu Tyr Trp Gly Gln Gly Thr Thr Val Thr
                     100             105
```